(12) United States Patent
Ling et al.

(10) Patent No.: US 8,691,578 B2
(45) Date of Patent: Apr. 8, 2014

(54) METHOD FOR GENERATING HOMOPLASMIC CELLS FROM HETEROPLASMIC CELLS

(75) Inventors: Feng Ling, Wako (JP); Takehiko Shibata, Wako (JP); Rong Niu, Tokyo (JP); Minoru Yoshida, Tokyo (JP); Yu-ichi Goto, Kodaira (JP)

(73) Assignees: National Center or Neurology and Psychiatry, Tokyo (JP); Riken, Saitama (JP)

( * ) Notice: Subject to any disclaimer, the term of this patent is extended or adjusted under 35 U.S.C. 154(b) by 155 days.

(21) Appl. No.: 12/965,195

(22) Filed: Dec. 10, 2010

(65) Prior Publication Data

US 2012/0040464 A1  Feb. 16, 2012

(30) Foreign Application Priority Data

Dec. 16, 2009  (JP) ................................. 2009-285729

(51) Int. Cl.
*C12N 15/01*  (2006.01)
*C07H 21/04*  (2006.01)

(52) U.S. Cl.
USPC ........................... 435/441; 435/325; 536/23.1

(58) Field of Classification Search
None
See application file for complete search history.

(56) References Cited

U.S. PATENT DOCUMENTS 7,736,895 B2  6/2010  Collas et al.

OTHER PUBLICATIONS

Santos, J.H. et al. The Journal of Biological Chemistry 278(3):1728 (2003).*
Ballana, E. et al. Human Mutation 29(2):248 (2008; published online Nov. 2007).*
Park, J.S. et al. Human Molecular Genetics 18(9):1578 (Feb. 2009).*
Wallace. Annu Rev Genet. 39, 359-407, 2005.
Ling and Shibata, EMBO J., 21, 4730-4740, 2005.
Ling et al., Mol. Cell. Biol., 27, 1133-1145, 2007.
Hori et al., Nucleic Acids Res., 37, 749-761, 2009.
Ling and Shibata, Mol. Biol. Cell, 15, 310-322, 2004.
Shibata and Ling, Mitochondrion, 7, 17-23, 2007.
Kirschner et al., Proc. Natl. Acad. Sci. USA., 60, 1466-1472, 1968.
Pohjoismaki et al., J. Biol. Chem., 284, 21446-21457, 2009.
Bogenhagen and Clayton, TIBS, 28, 357-360, 2003.
Bogenhagen and Clayton, TIBS, 28, 404-405, 2003.
Chen et al., Am. J. Hum. Genet., 57, 239-247, 1995.
Goto et al., Nature 348, 651-653, 1990.
Takahashi et al., Cell 2006, 126, 663-676, 2006.
Okita et al., Nature 448, 313-317, 2007.
Wernig et al., Nature 448, 318-324, 2007.
Maherali et al., Cell Stem Cell 1, 55-70, 2007.
Park et al., Nature 451, 141-146, 2007.
Nakagawa et al., Nature Biotech. 26, 101-106, 2008.
Wernig et al., Cell stem Cell 10, 10-12, 2008.
Yu et al., Science 318, 1917-1920, 2007.
Takahashi et al., Cell 131, 861-872, 2007.
Stadtfeld et al., Science 322, 945-949, 2008.
Zhou et al., Nature 455, 627-633, 2008.

* cited by examiner

*Primary Examiner* — Diana B Johannsen
(74) *Attorney, Agent, or Firm* — Pearne & Gordon LLP

(57) ABSTRACT

A method includes providing a eukaryotic cell including mutant mtDNA in which there is at least one mutation in the mtDNA, allowing the cell to come into contact with an active oxygen species or a chemical species that generates such an active oxygen species in the cell (e.g., hydrogen peroxide) and thereby changing the percentage of mutant mtDNA (mitochondrial genomic DNA) in the cell as a result of the contact. Also featured are cells obtained by the above-described method.

8 Claims, 3 Drawing Sheets

METHOD FOR GENERATING HOMOPLASMIC CELLS FROM HETEROPLASMIC CELLS

REFERENCE TO RELATED APPLICATION

The present application claims priority from Japanese Patent Application No. 2009-285729, filed on Dec. 16, 2009; the disclosure of which is hereby entirely incorporated by reference.

BACKGROUND OF THE INVENTION

1. Field of the Invention

The present invention relates to a method for changing the percentage of mutant mitochondrial genomic DNA in a cell. In addition, the present invention relates to a method for generating homoplasmic cells according to the above-described method.

2. Description of the Related Art

A eukaryotic cell comprises several hundreds of to several thousands of copies of mitochondrial DNA (hereinafter referred to as "mtDNA") in mitochondria thereof. Wild-type human mtDNA originally has a single genotype, namely, a single nucleotide sequence, in individual cells that constitute the whole body. This state is referred to as homoplasmy. To date, mitochondrial diseases such as mitochondrial myopathy, encephalopathy, lactic acidosis and stroke-like episodes (MELAS), chronic progressive external ophthalmoplegia (CPEO), myoclonic epilepsy with ragged-red fibers (MERRF)=Fukuhara disease, Leigh's encephalopathy, hypertrophic cardiomyopathy caused by mitochondrial DNA abnormity, Leber's disease, and Pearson syndrome have been known. There is no radical treatment for all these diseases. It has been known that, with regard to a majority of these mitochondrial diseases, mutant mtDNA coexists with wild-type mtDNA in a cell (this state is referred to as heteroplasmy), and that mitochondrial disease may be developed, when the percentage of such mutant mtDNA in the cell is high.

A person having mutant mtDNA was usually no symptom at birth. However, if the percentage of mutant mtDNA exceeds a certain threshold, clinical symptoms may be expressed. For example, it has been reported that most MELAS patients and some cardiomyopathy patients have a large mtDNA deletion of the nucleotide at position 3243, that most MERRF patients have a large mtDNA deletion of the nucleotide at position 8344, and that CPEO and Pearson syndrome patients also have a large deletion of the mtDNA thereof (Wallace, Annu Rev Genet., 39, 359-407, 2005). Moreover, it has been clarified that mutant mtDNA involving A3243G substitution may cause diabetes.

The aforementioned diseases caused by mutant mtDNA may all develop severe symptoms. However, at present, there have been no effective treatment. Thus, effective treatments have been strongly desired to be established as soon as possible.

If a heteroplasmic cell comprising both mutant mtDNA and wild-type mtDNA were converted to a homoplasmic cell having only normal mtDNA, it could provide an important key for developing the treatment of the mitochondrial diseases. To date, the present inventors have already revealed that only a moderate level of oxidative stress induces a special type of mtDNA replication (rolling circle DNA replication) (Ling and Shibata EMBO J., 21, 4730-4740, 2002; Ling et al., Mol. Cell. Biol., 27, 1133-1145, 2007), which is induced by the same mechanism as a homologous DNA recombination initiation mechanism in a budding yeast (*Saccharomyces cerevisiae*) (Hori et al., Nucleic Acids Res., 37, 749-761, 2009); and that homoplasmic cells can be generated from heteroplasmic cells by this rolling circle mtDNA replication (Ling and Shibata, Mol. Biol. Cell, 15, 310-322, 2004; Shibata and Ling, Mitochondrion, 7, 17-23, 2007).

On the other hand, it has been reported that mtDNA replication in mammalian cells including human cells is θ type replication (Kirschner et al., Proc. Natl. Acad. Sci. U.S.A., 60, 1466-1472, 1968). With regard to such mtDNA replication in mammalian cells including human cells, it has also been reported that a T4 phage type replication, in which recombination occurs together with replication, may be carried out (Pohjoismaki et al., J. Biol. Chem., 284, 21446-21457, 2009). At present, the details of such mechanisms have been in a state of chaos, and thus, have not yet been clarified. However, currently, it has been generally believed that rolling circle mtDNA replication is not a main mechanism (Bogenhangen and Clayton, Trends Biochem. Sci., 28, 357-360, 2003; Bogenhangen and Clayton, Trends Biochem. Sci., 28, 404-405, 2003).

In general, cells derived from a healthy human individual comprise wild-type mtDNA in a homoplasmic state. It has been reported that mtDNA deletions are present in egg cells collected from normal women (Chen et al., Am J Hum Genet, 57, 239 247, 1995). If this report is correct, it is considered that a fertilized egg can be converted to homoplasmic cells during the process of development and differentiation thereof. However, a mechanism for converting a fertilized egg to homoplasmic cells is totally unknown. Furthermore, as stated above, a mechanism for replicating mtDNA in mammalian cells including human cells differs from that for budding yeasts. Accordingly, it is not easy to predict a mechanism for converting mtDNA in mammalian cells to a homoplasmic state based on the mechanism for converting mtDNA in budding yeasts to a homoplasmic state.

Hence, in order to develop a method of medical treatment for mitochondrial diseases, it needs to promote further studies regarding the mechanisms for a homoplasmic state.

SUMMARY OF THE INVENTION

Under the above-mentioned circumstances, it is an object of the present invention to provide a method for changing the percentage of mutant mtDNA in a cell.

Moreover, it is another object of the present invention to provide a method for generating homoplasmic cells according to the above-described method.

Furthermore, it is another object of the present invention to provide the cells in which the percentage of mutant mtDNA has been changed, and processed homoplasmic cells.

The present inventors have found that the percentage of mutant mtDNA in a eukaryotic cell can be unexpectedly changed by allowing the eukaryotic cell to come into contact with a reactive oxygen species (ROS), and further that homoplasmic cells comprising mtDNA having a standard sequence can be prepared, thereby completing the present invention.

Specifically, the present invention comprises the following (1) to (12):

(1) A method, which comprises allowing a eukaryotic cell to come into contact with a reactive oxygen species or a chemical species that generates such a reactive oxygen species in the cell, and thereby changing the percentage of mutant mtDNA in the cell.

(2) The method according to (1) above, wherein the reactive oxygen species is one selected from the group consisting of single oxygen, superoxide anion radical, hydrogen peroxide and hydroxy radical, or a combination thereof (3) The method according to (1) above, wherein the chemical species that generates such a reactive oxygen species in the cell is one selected from the group consisting of hydrogen peroxide, iron(II) chloride, alloxan and antimycin, or a combination thereof (4) The method according to (2) or (3) above, wherein the reactive oxygen species or the chemical species that generates such a reactive oxygen species in the cell is hydrogen peroxide.

(5) The method according to any one of (1) to (4) above, wherein the time required for allowing the eukaryotic cell to come into contact with the reactive oxygen species or the chemical species that generates such a reactive oxygen species in the cell is 10 minutes to 1 hour.

(6) The method according to any one of (1) to (5) above, which is characterized in that it comprises changing the percentage of the mutant mtDNA in the cell to 5% or less.

(7) A method for preparing cells, in each of which the percentage of mutant mtDNA has been changed, by applying the method according to any one of (1) to (6) above.

(8) A method for preparing homoplasmic cells by applying any one of the method according to any one of (1) to (6) above.

(9) The method according to (8) above, which is characterized in that the homoplasmic cells comprise only wild-type mtDNA.

(10) A cell prepared by the method according to any one of (7) to (9) above.

(11) An iPS cell prepared from the cell according to (10) above.

(12) A cell having a cell type different from that of the cell according to (10) above, which is prepared from the cell according to (10) above without involving an iPS cell.

Effects of the Invention

According to the present invention, the percentage of mutant mtDNA in a cell can be changed. Moreover, according to the present invention, there can be provided a cell in which the percentage of mutant mtDNA has been changed, or a homoplasmic cell (for example, a homoplasmic cell comprising only wild-type mtDNA).

iPS cells prepared from the homoplasmic cells comprising only wild-type mtDNA, which are prepared by the method of the present invention, can be used for the regeneration of various tissues causing dysfunction to people with mitochondrial disease or mitochondrial diabetes. Alternatively, differentiated cells, which are prepared by allowing the homoplasmic cells comprising only wild-type mtDNA prepared by the method of the present invention to differentiate into specific tissue cells without involving iPS cells, can also be used for the regeneration of tissues.

Accordingly, the present invention is extremely effective for providing tissue materials used for the treatment of diseases caused by mutant mtDNA.

Moreover, since the homoplasmic cells prepared by the method of the present invention have a predisposition for being converted to heteroplasmic cells, they have a high potential as a useful tool for clarifying a mechanism for converting homoplasmic cells to heteroplasmic cells. That is to say, the homoplasmic cells prepared by the method of the present invention can be used to clarify a mechanism for the development of a disease caused by a newly occurred mutation of mtDNA.

Furthermore, according to the present invention, it is also possible to increase the percentage of mutant mtDNA in a cell. Thus, in a case in which the percentage of mutant mtDNA is lower than the detection limit, the presence or absence of a predisposition for a disease caused by the mutation of mtDNA can be confirmed in advance by amplifying mutant DNA, which exists in a trace amount in a cell, according to the method of the present invention.

The longitudinal axis in the upper view indicates the percentage (%) of the A3243G substitution mutant, and the horizontal axis corresponds to clone numbers (clones) used in the lower view. In addition, the term "MELAS bulk" used in the lower view is relevant to MELAS cells before cloning, and it shows the results obtained by analyzing the percentage of the A3243G substitution mutant.

Figure 1:
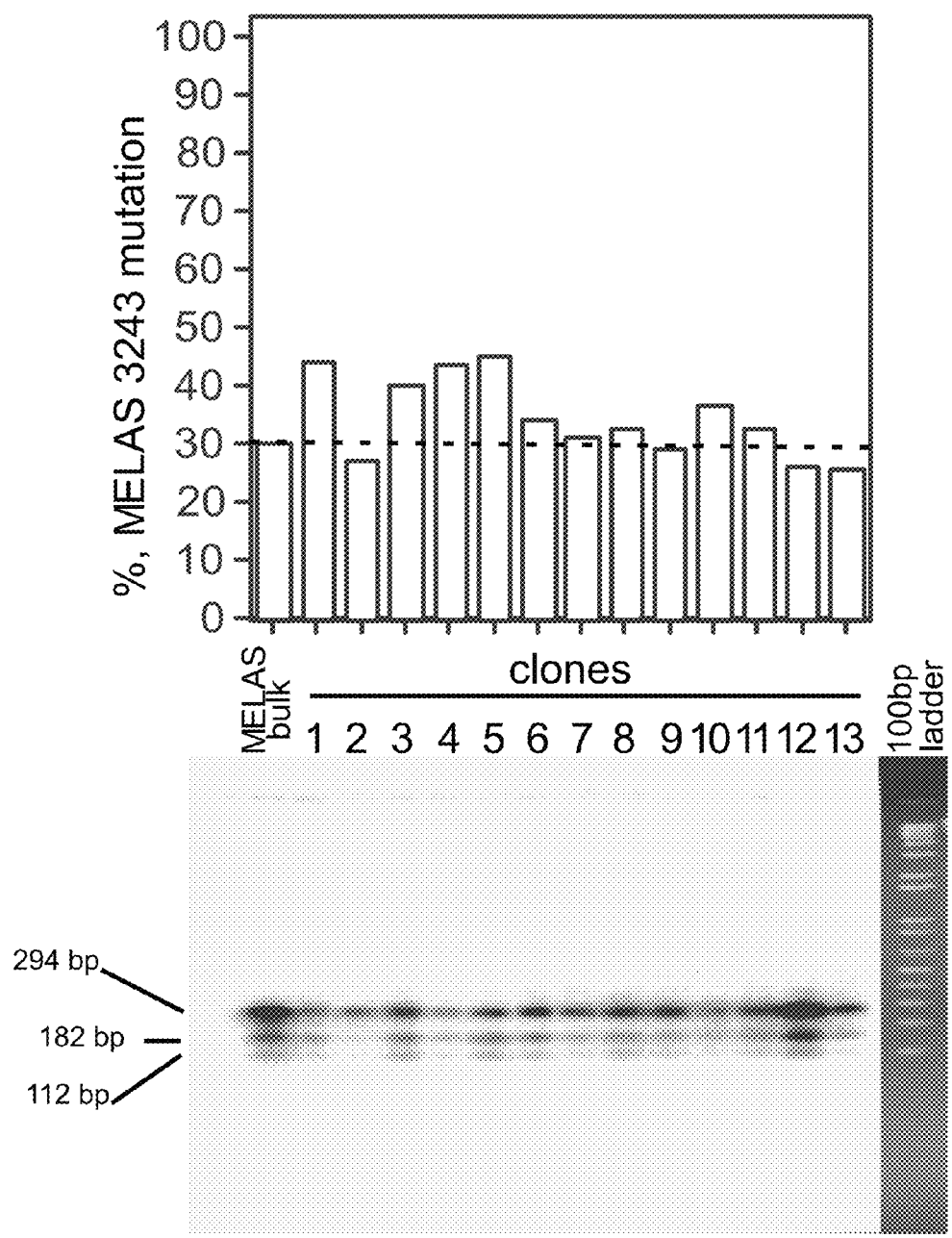
FIG. 1 shows the results obtained by analyzing the heteroplasmic state of primary culture cells from MELAS patients having A3243G substitution mutant mtDNA. The lower view shows the results obtained by treating a fragment around the nucleotide at position 3243 obtained from each cell clone with ApaI and then subjected to agarose gel electrophoresis. The upper view is a graph obtained by the numerical conversion of the percentage of A3243G substitution mutant mtDNA existing in each cell clone, based on the results shown in the lower view. A band of 294 bp is derived from wild-type mtDNA, and bands of 182 bp and 112 bp are derived from A3243G substitution mutant mtDNA (lower view).
Figure 2:
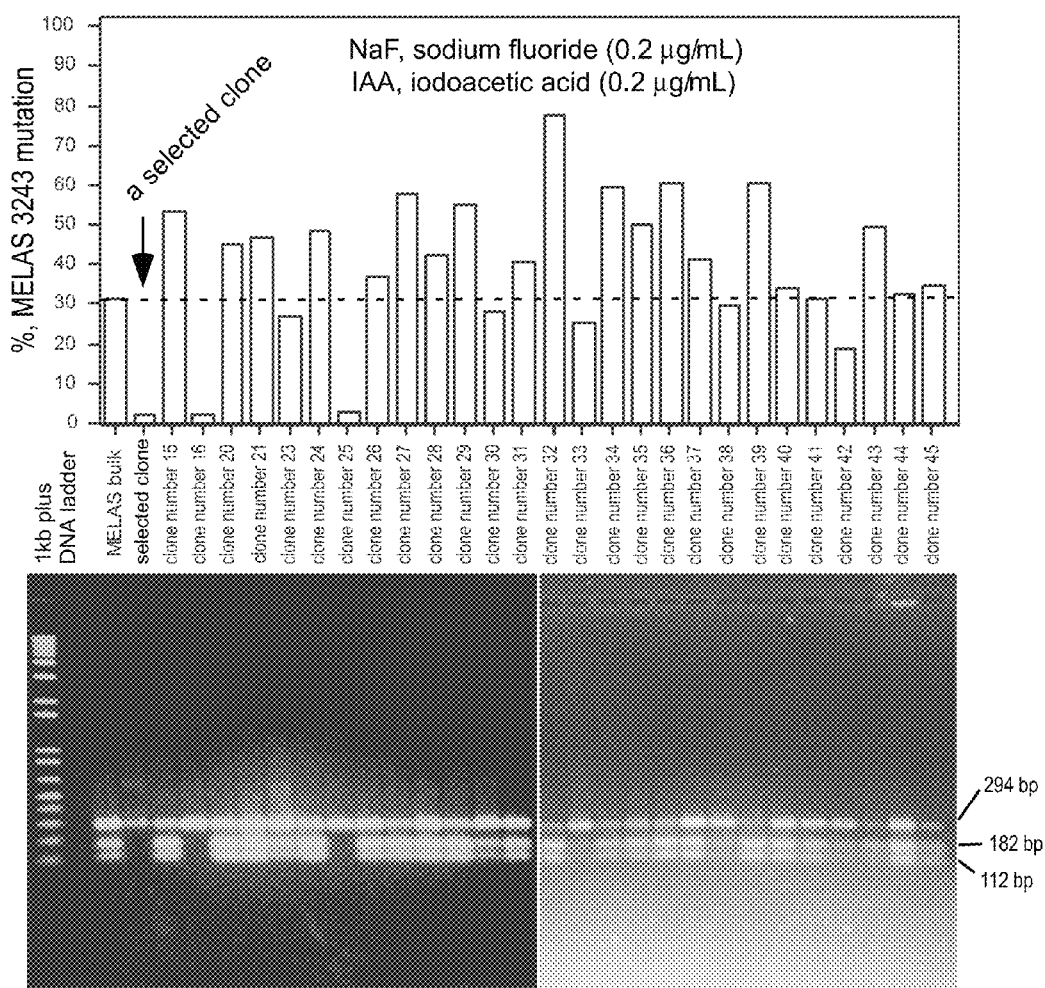

FIG. 2 shows the results obtained by analyzing the state of heteroplasmic cells, which have been treated with hydrogen peroxide. The cells were treated with hydrogen peroxide, and they were then analyzed in the same manner as that in FIG. 1.

Figure 3:
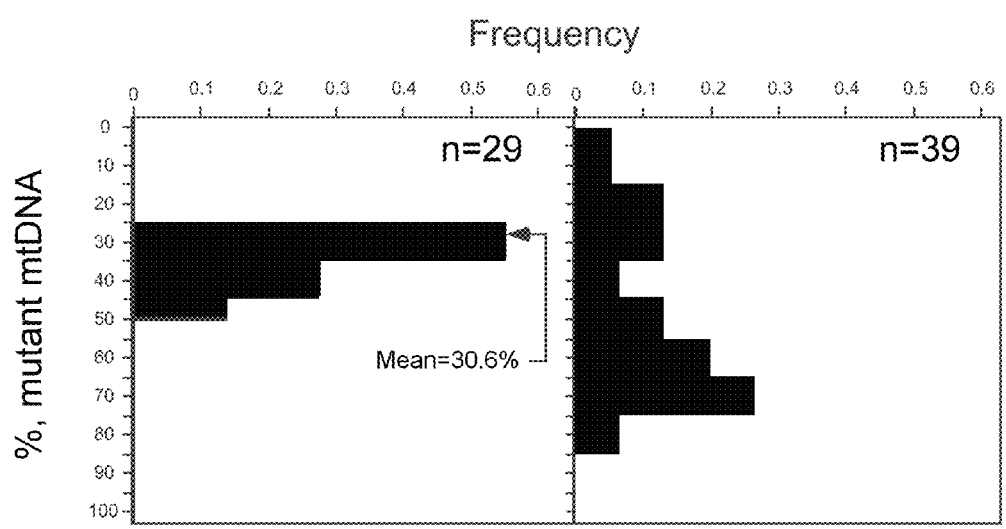

FIG. 3 shows the results obtained by converting cells to a homoplasmic state by a hydrogen peroxide treatment. In the case of not treating the cells with hydrogen peroxide (left view), the percentage of mutant mtDNA was distributed in a narrow range. On the other hand, in the case of treating the cells with hydrogen peroxide (right view), the percentage of mutant mtDNA was distributed in two peaks. Separation into the two peaks indicates that wild-type mtDNA and mutant mtDNA were each transferred to their homoplasmies. A portion thereof indicates homoplasmic cells comprising almost only normal mtDNA. Since a homoplasmy comprising only mutant mtDNA is considered fatal, it is excluded from the analysis results.

DETAILED DESCRIPTION OF THE INVENTION

On embodiment of the present invention relates to a method, which comprises allowing a eukaryotic cell to come into contact with a reactive oxygen species or a chemical species that generates such a reactive oxygen species in the cell, and thereby changing the percentage of mutant mtDNA in the cell.

The type of the eukaryotic cell used in the present invention is not particularly limited. For example, mammalian cells are used. Among others, cells from humans and non-human animals are preferable. Examples of such cells include cells from a mouse, a rat, a bovine, a horse, a swine, a sheep, a monkey, a dog, a cat and a bird. Human-derived cells are particularly preferable. Moreover, the eukaryotic cells used in the present invention are particularly preferably cells having mutant mtDNA or cells suspected to have mutant mtDNA.

The term "a reactive oxygen species" is used herein to mean an oxygen species, which is chemically activated. Such a reactive oxygen species includes all of chemical species, which are generally understood by persons skilled in the art. Examples of such a reactive oxygen species include, but are not particularly limited to, superoxide anion radical, hydroxy radical, hydrogen peroxide, single oxygen, nitrogen monoxide, nitrogen dioxide, ozone and peroxylipid. It is preferable to select the type or amount of a chemical species, which does not cause damage to cells, or a chemical species, which is capable of having a means for reducing damage to cells, although it may cause such damage to the cells. Preferred reactive oxygen species include superoxide anion radical, hydroxy radical, hydrogen peroxide, single oxygen and the like. On the other hand, the term "a chemical species that generates a reactive oxygen species in a cell" is used herein to mean a chemical species, which generates a reactive oxygen species in a cell, after it has entered the cell and has caused a chemical reaction in the cell, depending on the type of the chemical species. Examples of such a chemical species that generates a reactive oxygen species in a cell include, but are not limited to, iron(II) chloride ($FeCl_2$), alloxan and antimycin.

Moreover, the expression "allowing . . . to come into contact with" from the description "allowing a eukaryotic cell to come into contact with a reactive oxygen species or a chemical species that generates such a reactive oxygen species in the cell" is used herein to mean that a reactive oxygen species or a chemical species that generates such a reactive oxygen species in a cell is allowed to be present in a medium or the like, in which a cell of interest grows, so that the reactive oxygen species or the chemical species that generates the reactive oxygen species in the cell can enter the cell of interest, and that the reactive oxygen species or the chemical species that generates the reactive oxygen species in the cell is then treated, so that it can be contacted with the cell. The reactive oxygen species or the chemical species that generates the reactive oxygen species in a cell may be of a single species, or of multiple species. Furthermore, the reactive oxygen species may be combined with the chemical species that generates the reactive oxygen species in a cell, and the obtained mixture may be then added to a medium.

With regard to an amount of a reactive oxygen species, the amount of a reactive oxygen species, which enters or is generated in a cell as a result of the addition of hydrogen peroxide in a concentration of 50 µM to 400 µM, is preferably applied. The amount of a reactive oxygen species present in a medium can be measured, as appropriate, by persons skilled in the art. For example, the amount of a reactive oxygen species present in a medium can be measured using a commercially available fluorescent probe (CM-$H_2$DCFDA; Molecular Probes). For example, in a case in which hydrogen peroxide is added to a medium, it is necessary to add it in an amount that does not cause damage to cells used. Such an amount can be easily calculated by persons skilled in the art by previously conducting preliminary experiments. When hydrogen peroxide is used as a reactive oxygen species, the concentration of the hydrogen peroxide in a medium is, for example, 50 µM to 400 µM, more preferably 70 µM to 300 µM, further preferably 90 µM to 200 µM, and particularly preferably approximately 100 µM.

When a chemical species that generates a reactive oxygen species in a cell is added to a medium, chemical species such as iron(II) chloride ($FeCl_2$) (having a concentration to be added to a medium of, for example, 1 µM to 30 µM, preferably 5 µM to 20 µM, and more preferably approximately 10 µM), alloxan (having a concentration to be added to a medium of, for example, 1 mM to 30 mM, preferably 5 mM to 20 mM, and more preferably approximately 10 mM), or antimycin (having a concentration to be added to a medium of, for example, 10 µM to 500 µM, preferably 50 µM to 300 µM, more preferably 100 µM to 250 µM, and further preferably approximately 200 µM), can be added to the medium, but the examples of such chemical species are not limited thereto. When such a chemical species that generates a reactive oxygen species in a cell is added to a medium, the additive amount of the chemical species can also be easily determined by previously examining damage given to cells.

The time required for allowing a reactive oxygen species or a chemical species that generates such a reactive oxygen species in a cell to come into contact with the cell can be calculated, for example, as a processing time at which a reactive oxygen species or a chemical species that generates such a reactive oxygen species (e.g. iron(II) chloride, alloxan, antimycin, etc.) in a cell is allowed to be present in a medium containing the cell. Such a processing time is a time, which does not cause damage to the cell used, and which is effective for treating the cell with a reactive oxygen species or a chemical species that generates such a reactive oxygen species in the cell. The processing time depends on a reactive oxygen species or a chemical species that generates such a reactive oxygen species in a cell to be used. It is, for example, 1 minute to 2 hours, or 5 minutes to 1.5 hours, preferably 10 minutes to 1 hour, and more preferably approximately 30 minutes, but the examples of such a processing time are not limited thereto.

The "mutant mtDNA" in the present embodiment means mtDNA having a sequence different from a standard sequence. The number of mutation sites existing in a single mtDNA is one or several sites, preferably 1 to 3 sites, and more preferably 1 site. Moreover, the type of the "mutation" on mutant mtDNA is not particularly limited, and it includes all mutations, which are different from a standard sequence. Particularly preferably, it is a mutation, which causes a certain disease (for example, substitution mutations regarding the nucleotide at position 3243 (a causal mutation for MELAS), the nucleotide at position 8344 (a causal mutation of MERRF), etc.; see Non-Patent Document 1 for the details).

A change in the percentage of mutant mtDNA in a cell may be either an increase or a decrease. For example, when the percentage of mutant mtDNA which causes a disease is low to such an extent that the percentage of the mutant mtDNA cannot be detected by an ordinary method, the presence or absence of a predisposition for the disease can be determined by increasing the percentage of the mutant mtDNA according to the present invention. Accordingly, the present invention includes a method for determining the possibility of being affected by a disease caused by the mutation of mtDNA, which is lower than the detection limit.

Moreover, homoplasmic cells (as described later) can be prepared by reducing the percentage of mutant mtDNA in a cell to the minimum.

A change in the percentage of mutant mtDNA in a cell can be easily determined, for example, using a restriction enzyme whose cleavage sensitivity differs depending on the presence or absence of a mutation (see, for example, Goto et al., Nature, 348, 651-653, 1990, etc.). In addition to the aforementioned method, other methods, such as an allele-specific PCR method, a quantitative PCR method, an invader method, and an analysis method using a next-generation sequencer, may also be applied.

With regard to the "percentage of mutant mtDNA in a cell" changed by the present invention, when the percentage is decreased, the percentage of mutant mtDNA reduced is, for example, 30% or less, preferably 20% or less, more preferably 10% or less, further preferably 5% or less, and most preferably 0%. On the other hand, when the percentage is increased, the percentage of mutant mtDNA increased is, for example, 10% or more, 20% or more, 30% or more, 40% or more, 50% or more, or 60% or more; preferably 70% or more, or 80% or more; more preferably 90% or more; and further preferably 95% or more.

Another embodiment of the present invention relates to a "cell, in which the percentage of mutant mtDNA has been changed to a desired percentage," which is prepared as a result of allowing a eukaryotic cell to come into contact with a reactive oxygen species or a chemical species that generates such a reactive oxygen species in the cell, or a "homoplasmic cell."

The term "homoplasmy" means that the nucleotide sequence of mtDNA is in a uniform state at a cell or individual animal level. In contrast, a state in which the nucleotide sequence of mtDNA is not uniform at a cell or individual animal level is referred to as "heteroplasmy." For example, when the nucleotide sequence of mtDNA contained in a certain cell (or individual animal) is uniform in all mitochondrial genomic copies, the certain cell (or individual animal) is a "homoplasmic cell (or individual animal)." In the present specification, a cell (or an individual animal), which uniformly comprises a standard mtDNA sequence, is particularly referred to as a "wild-type homoplasmic cell (or individual animal)" or a "homoplasmic cell comprising only wild-type mtDNA," or the like. Further, by focusing on a specific mutation present on mtDNA, when the nucleotide sequence of the mutation site is uniform at a cell or individual animal level, it is referred to as a "homoplasmic state" with regard to the specific mutation in the present specification.

Still further, the term "homoplasmy" is used in the present specification to mean a state in which the percentage of mtDNA copies each having the same nucleotide sequence in a cell is 90% or more, particularly preferably 95% or more, and most preferably 99% or more (wherein the percentage of mutant mtDNA is 1% or less).

A cell in which the percentage of mutant mtDNA has been changed, or a homoplasmic cell, can be selected and prepared by a method well known to persons skilled in the art. For example, single colonies are formed from a cell, which has been treated with a reactive oxygen species or a chemical species that generates such a reactive oxygen species in the cell, according to a suitable method (e.g. limiting dilution, etc.), and a DNA sample is then prepared from cell clones from the obtained single colonies. By confirming the intracellular percentage of mutant mtDNA in the prepared DNA sample, cell clones with a desired percentage can be selected. When wild-type homoplasmic cells are selected, if selection is carried out in the presence of a suitable drug for inhibiting a glycolytic system (e.g. sodium fluoride, iodoacetic acid, etc.), wild-type homoplasmic cells can be more easily selected.

The "cell in which the percentage of mutant mtDNA has been changed" includes both a cell in which the percentage of mutant mtDNA has been increased, and a cell in which the percentage of mutant mtDNA has been decreased. For instance, the cell in which the percentage of mutant mtDNA has been decreased is a cell in which the percentage of mutant mtDNA is, for example, 30% or less, preferably 20% or less, more preferably 10% or less, further preferably 5% or less, and most preferably 0%. On the other hand, the cell in which the percentage of mutant mtDNA has been increased is a cell in which the percentage of mutant mtDNA is, for example, 10% or more, 20% or more, 30% or more, 40% or more, 50% or more, or 60% or more; preferably 70% or more, or 80% or more; more preferably 90% or more; and further preferably 95% or more.

The present invention also includes: a method for preparing a cell having a different cell type, from a cell in which the percentage of mutant mtDNA has been changed to a desired percentage, which is prepared by the method of the present invention, or from a homoplasmic cell; and a cell prepared by the above-described method.

Such methods for preparing a cell having a different cell type include: a method, which comprises preparing an iPS cell from a cell in which the percentage of mutant mtDNA has been changed to a desired percentage, which is prepared by the method of the present invention, or from a homoplasmic cell, and then inducing the differentiation of the iPS cell into a cell having a desired cell type, which is in a desired differentiation state; a method for directly preparing a cell having a desired cell type without involving an iPS cell; and other methods.

The iPS cell is a cell, which has acquired pluripotent differentiation potential equivalent to that of an ES cell as a result of the introduction of several types of transcriptional factor genes imparting pluripotent differentiation potential to somatic cells, transcriptional factor proteins, compounds inducing such pluripotent differentiation potential, and the like (which are generically referred to as pluripotent differentiation factors). Many factors have already been reported as such pluripotent differentiation factors. Examples of such pluripotent differentiation factors include, but are not limited to, an Oct family (e.g. Oct3/4), a SOX family (e.g. SOX2, SOX1, SOX3, SOX15, SOX17, etc.), a Klf family (e.g. Klf4, Klf2, etc.), a MYC family (e.g. c-MYC, N-MYC, L-MYC, etc.), NANOG, and LIN28. Many publications have disclosed methods for establishing iPS cells. Thus, for detailed information about method for establishing iPS cells, such publications can be referred to (see, for example, Takahashi et al., Cell 2006,126: 663-676; Okita et al., Nature 2007, 448: 313-317; Wernig et al., Nature 2007, 448: 318-324; Maherali et al., Cell Stem Cell 2007, 1: 55-70; Park et al., Nature 2007, 451: 141-146; Nakagawa et al., Nat Biotechnol 2008, 26: 101-106; Wernig et al., Cell Stem Cell 2008,10: 10-12; Yu et al., Science 2007, 318: 1917-1920; Takahashi et al., Cell 2007, 131: 861-872; Stadtfeld et al., Science 2008 322: 945-949; etc.).

A gene encoding a pluripotent differentiation factor is introduced into a homoplasmic cell prepared by the method of the present invention, and the above-mentioned publications are then referred to for further information, so that an iPS cell can be established. When various types of tissues or cells obtained by inducing the differentiation of the thus established iPS cells are transplanted into an individual, from which homoplasmic cells are derived, they are able to solve a problem regarding histoincompatibility. Accordingly, such tissues or cells can be used as effective materials for treating mitochondrial diseases and the like.

Moreover, as a method for directly preparing a cell having a desired cell type without involving an iPS cell, for example, there has been reported a method of allowing a specific transcriptional factor to express in a cell, so as to convert the cell to a cell having a desired cell type (Zhou et al., Nature 455, 627-633, 2008). This report has disclosed a method of allowing three types of genes (Ngn3, Pdx1 and Mafa) are allowed to express in a pancreatic exocrine cell, so as to convert the cell to a β cell. In addition, there has also been reported a method of incubating any given permeable cell together with an interphase cell extract or a mitotic division cell extract, so as to convert the any given cell to a cell having a desired cell type (U.S. Pat. No. 7,736,895). If such methods were applied to a wild-type homoplasmic cell prepared by the method of the present invention, a cell, which has a desired cell type and does not have mutant mtDNA that causes mitochondrial diseases and other diseases, could be prepared. The thus prepared cell can be transplanted into tissues, which are affected by the mutation of mtDNA, and thus it can be used for the treatment of diseases caused by mutant mtDNA.

The type of a cell having a desired cell type, which is prepared from the homoplasmic cell of the present invention, is not particularly limited, as long as it is adequate for purposes such as treatment and the like. Preferred examples of such a cell having a desired cell type include a nerve cell, a striated muscle cell, a smooth muscle cell, an epithelial cell, an epidermal cell, a corneocyte, a hematopoietic cell, a melanocyte, a chondrocyte, a retinal epithelial cell, a β cell, a cardiac muscle cell, a B cell, a T cell, blood system cells (an erythrocyte, a leukocyte, a thrombocyte, etc.), and a fibroblast.

EXAMPLES

Using heteroplasmic cells from mitochondrial disease patients as an example, a method for changing the percentage of mutant mtDNA in such a cell will be described in the present examples. The following examples are provided only for illustrating a part of the present invention. Thus, cases in which cells other than those described in the present examples, reactive oxygen species other than those described in the present invention and others are used, are naturally included in the scope of the present invention.

1. Verification of Safety of Heteroplasmic Cells

It was confirmed that A3243G substitution mutation of mtDNA causes the onset of a mitochondrial disease, MELAS. Hence, verification was carried out on the heteroplasmic state of A3243G substitution mutation present in the mtDNA of primary culture cells from the skeletal muscle and skin of MELAS patients (wherein the cells were prepared by Dr. Yuichi GOTO, the National Center of Neurology and Psychiatry, and hereinafter, the cells are referred to as MELAS cells).

MELAS cells were plated to result in a cell density of $1 \times 10^5$ to $1 \times 10^6$ cells/mL in the presence of DMEM containing 10% FCS, and they were then cultured at 37° C. in a 5% $CO_2$ atmosphere for 3 days. After completion of the culture for 3 days, when the cell density reached $5 \times 10^5$ to $6 \times 10^6$ cells/mL, the cells were diluted by a factor of $10^4$ to $1.2 \times 10^5$. The resultant cells were plated and were further cultured for 15 days. After completion of the culture for 15 days, several single colonies of cells were selected, and DNA was then extracted by a common method. Using the extracted DNA sample as a template, PCR was carried out with a primer pair for amplifying a site around the nucleotide at position 3243 of the mtDNA. Thereafter, the PCR product was treated with ApaI. In the case of normal mtDNA, the sequence around the nucleotide at position 3243 is GAGCCC (wherein the underlined portion corresponds to the nucleotide at position 3243). However, in the case of the mtDNA of MELAS patients, the sequence is changed to GGGCCC (wherein the underlined portion corresponds to the nucleotide at position 3243) due to mutation, and as a result, it exhibits sensitivity to a treatment with ApaI. Since a PCR product from normal mtDNA does not contain an ApaI recognition sequence, only a single DNA band (a 294-bp band in the present examples) is detected even after a treatment with ApaI. On the other hand, a PCR product from mutant mtDNA becomes sensitive to ApaI, and as a result, two bands cleaved with ApaI are detected (182-bp and 112-bp bands in the present examples) (see the lower view of FIG. 1). Accordingly, it becomes possible to evaluate the heteroplasmic state of the cells by calculating the ratio of the 182-bp and 112-bp bands to the 294-bp bands (see Goto et al., Nature, 348, 651-653, 1990 for the details of this method).

FIG. 1 shows the results obtained by analyzing the percentage of A3243G substitution mutation in several cell clones obtained from a MELAS cell line. It was confirmed that the heteroplasmic state of cell clones obtained from cells from MELAS patients was generally stable (approximately 30%) (the upper view of FIG. 1).

2. Influence of treatment with reactive oxygen species on percentage of mutant mtDNA Next, the influence of hydrogen peroxide on the heteroplasmic state of the aforementioned MELAS cells was examined, in a case in which the hydrogen peroxide used as a reactive oxygen species was allowed to come into contact with the MELAS cells.

Hydrogen peroxide was added to a medium containing the MELAS cells (cell density: $1 \times 10^5$ to $1 \times 10^6$ cells/mL) to a final concentration of 100 µM, and the obtained mixture was then cultured at 37° C. in a 5% $CO_2$ atmosphere for 30 minutes. Thereafter, the cells were washed with PBS three times, and were then cultured for 3 days. After completion of the culture for 3 days, when the cell density reached $5 \times 10^5$ to $6 \times 10^6$ cells/mL, the cells were diluted by a factor of $10^4$ to $1.2 \times 10^5$. The resultant cells were plated and were further cultured for 15 days. After completion of the culture for 15 days, several single colonies of cells were selected, and DNA was then extracted by a common method. The intracellular percentage of the A3243G substitution mutation of mtDNA was examined with respect to the obtained DNA samples by the same method as described above.

FIG. 2 shows the results obtained by analyzing the percentage of A3243G substitution mutation present in each cell clone obtained after a hydrogen peroxide treatment. When the cells were treated with hydrogen peroxide, cell clones with almost 0% of A3243G substitution mutation could be obtained (for example, clone 16, clone 25, etc.; see the upper view of FIG. 2). When normal homoplasmic cells each having 0% of A3243 substitution mutation are selected, if a drug for inhibiting a glycolytic system, such as sodium fluoride (for example, 0.2 µg/mL) or iodoacetic acid (for example, 0.2 µg/mL), is added, normal homoplasmic cells can be more easily selected (the upper view of FIG. 2, "selected clone").

Furthermore, the presence of clones, in which the percentage of A3243G substitution mutation became higher than the case of not treating with hydrogen peroxide (30%), could also be confirmed (e.g. clones 15, 27, 29, 32, 34, 35, 36, 39, etc.; the upper view of FIG. 2). These results suggest that the percentage of mutant mtDNA in a cell can be increased or decreased by treating the cell with a reactive oxygen species. Hence, in order to further analyze this point, cell clones from cells that had been treated with hydrogen peroxide and cell clones from cells that had not been treated with hydrogen peroxide were examined in terms of distribution of the percentages of mtDNAs having A3243G substitution mutation in cells. The left view of FIG. 3 shows the results obtained by examining cell clones from MELAS cells selected without being treated with hydrogen peroxide, in terms of the percentages of A3243G substitution mutations in the cell clones. The percentages of the A3243G substitution mutations of the cell clones that had not been treated with hydrogen peroxide were distributed to a narrow range from approximately 25% to 50%. In contrast, it could be confirmed that, in the case of cell clones that had been treated with hydrogen peroxide, distribution of the percentages of the substitution mutations was divided into two ranges, namely, a range from 0% to 40% and a range from 40% to 80%. These results demonstrate that A3243 substitution mutations are uniformized to be increased or decreased by treating the cells with hydrogen peroxide.

As described above, it became clear that the treatment of cells with hydrogen peroxide (treatment with a reactive oxygen species) promotes the conversion of the cells to a homoplasmic state.

Industrial Applicability

According to the present invention, the percentage of mutant mtDNA in a cell can be changed. Thus, it becomes possible to produce, for example, a homoplasmic cell, which comprises only wild-type mtDNA and which does not comprise mutant mtDNA causing diseases. At present, a method for completely treating mitochondrial diseases caused by the mutation of mtDNA has not yet been discovered. Under such circumstances, the present invention greatly contributes to the development of materials and methods for treating the aforementioned diseases in the field of regenerative medicine and the like.

What is claimed is:

1. A method comprising
providing a eukaryotic cell including mutant mtDNA in which there is at least one mutation in the mtDNA that causes a mitochondrial disease, wherein the percentage of mutant mtDNA in said cell is known;
contacting said cell or a clone of said cell with a reactive oxygen species or a chemical species that generates such a reactive oxygen species;
thereby changing, as a result of said contact, the percentage of mutant mtDNA in said cell or said clone that includes the at least one mutation;
determining the percentage of the mutant mtDNA in said cell or said clone; and
obtaining said cell or said clone having a desired percentage of the mutant mtDNA.

2. The method of claim 1 wherein said cell is obtained from a patient having a mitochondrial disease.

3. The method of claim 1 wherein said desired percentage of the mutant mtDNA is 5% or less.

4. The method of claim 1 wherein said desired percentage of the mutant mtDNA is 0%.

5. The method of claim 1 wherein said percentage of the mutant mtDNA in said cell or said clone is determined by a method selected from the group consisting of: using a restriction enzyme whose cleavage specificity depends on the presence or absence of the mutation, an allele-specific PCR method, a quantitative PCR method, an invader method and an analysis method using a next-generation sequencer.

6. The method of claim 1 comprising forming iPS cells from said obtained cell or said obtained clone.

7. The method of claim 4 comprising forming iPS cells from said obtained cell or said obtained clone which are capable of being differentiated into tissue or differentiated cells.

8. The method of claim 4 comprising converting said obtained cell or said obtained clone into a cell having a different cell type.

* * * * *

UNITED STATES PATENT AND TRADEMARK OFFICE
CERTIFICATE OF CORRECTION

| | | |
|---|---|---|
| PATENT NO. | : 8,691,578 B2 | Page 1 of 1 |
| APPLICATION NO. | : 12/965195 | |
| DATED | : April 8, 2014 | |
| INVENTOR(S) | : Feng Ling et al. | |

It is certified that error appears in the above-identified patent and that said Letters Patent is hereby corrected as shown below:

On the Title Page, item (73) in the patent details, "Assignee," please delete "National Center or Neurology and Psychiatry" and insert -- National Center of Neurology and Psychiatry --

Signed and Sealed this
Twenty-ninth Day of July, 2014

Michelle K. Lee
*Deputy Director of the United States Patent and Trademark Office*